United States Patent [19]
Münger et al.

[11] Patent Number: 5,736,318
[45] Date of Patent: Apr. 7, 1998

[54] METHOD AND KIT FOR EVALUATING HUMAN PAPILLOMAVIRUS TRANSFORMED CELLS

[75] Inventors: Karl Münger, Brookline; D. Leanne Jones, Somerville, both of Mass.

[73] Assignees: President and Fellows of Harvard College; Harvard University, Office of Technology Transfer, both of Cambridge, Mass.

[21] Appl. No.: 406,248

[22] Filed: Mar. 17, 1995

[51] Int. Cl.$^6$ ............... C12Q 1/70; C12N 9/00; A61K 39/12; C07K 1/00
[52] U.S. Cl. ............ 435/5; 435/183; 424/204.1; 424/277.1; 530/395
[58] Field of Search .............. 435/5, 183; 424/204.1, 424/277.1; 530/395

[56] References Cited

FOREIGN PATENT DOCUMENTS

| | | |
|---|---|---|
| 0 523 391 A1 | 1/1993 | European Pat. Off. |
| 0 531 080 A2 | 3/1993 | European Pat. Off. |
| WO92/11290 | 7/1992 | WIPO |
| WO93/20844 | 10/1993 | WIPO |
| WO 94/17413 | 8/1994 | WIPO |

OTHER PUBLICATIONS

Slebos et al. (1994) *Proc. Natl. Acad. Sci. USA* 91:5320–5324.
Demers et al. (1994) *Proc. Natl. Acad. Sci. USA* 91:4382–4386.
Xiong et al. (1993) *Genes & Development* 7:1572–1583.
Harper et al. (1993) *Cell* 75:805–816.
El–Deiry et al. (1993) *Cell* 75:817–825.
Dyson et al. (1992) *Journal of Virology* 6893–6902.
White et al. (1994) *Genes & Development* 8:666–677.
Hunter et al. (1994) *Cell* 79:573–582.
Vousden et al. (1993) *Oncogene* 8:1697–1702.
Munger et al. (1989) *The EMBO Journal* 8:4099–4105.
Xiong et al. (1993) *Nature* 366:701–704.
Xiong Y. et al Subunit rearrangement of the cyclon–dependent kinase is associated with cellular transformation. Genes & Development 7:1572–1583 1993.
Vousden, K.A. Human Papillomaviruses & Cervical Cancer. Stern P L et al New York, Ny. 1994 Oxford Univ. Press p. 92.

*Primary Examiner*—Marian C. Knode
*Assistant Examiner*—Ali R. Salimi
*Attorney, Agent, or Firm*—Hale and Dorr LLP

[57] ABSTRACT

The invention provides methods and kits for determining the extent of interaction and/or inactivation between a cyclin/cyclin-dependent kinase inhibitor and the human papilomavirus E7 oncoprotein and thus for evaluating the proliferative state of a transformed cell. Methods for identifying compounds capable of inhibiting the interaction between a cyclin/cyclin-dependent kinase inhibitor and the human papilomavirus E7 oncoprotein, and for inhibiting growth of a human papillomavirus-associated carcinoma cell are also provided.

1 Claim, 2 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 495 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: Homo sapiens
        ( B ) STRAIN: WI38

( i x ) FEATURE:
        ( A ) NAME/KEY: CDS
        ( B ) LOCATION: 1..495

( x ) PUBLICATION INFORMATION:
        ( A ) AUTHORS: Xiong, Y.
                Hannon, G. J.
                Zhang, H.
                Casso, D.
                Kobayashi, R.
                Beach, D.
        ( B ) TITLE: p21 is a Universal Inhibitor of Cyclin Kinase
        ( C ) JOURNAL: Nature
        ( D ) VOLUME: 366
        ( E ) ISSUE: 6456
        ( F ) PAGES: 701-704
        ( G ) DATE: 1993
        ( K ) RELEVANT RESIDUES IN SEQ ID NO:1: FROM 1 TO 495

( x i ) SEQUENCE DESCRIPTION: SEQ ID NO:1:

```
ATG TCA GAA CCG GCT GGG GAT GTC CGT CAG AAC CCA TGC GGC AGC AAG      48
Met Ser Glu Pro Ala Gly Asp Val Arg Gln Asn Pro Cys Gly Ser Lys
 1               5                  10                  15

GCC TGC CGC CGC CTC TTC GGC CCA GTG GAC AGC GAG CAG CTG AGC CGC      96
Ala Cys Arg Arg Leu Phe Gly Pro Val Asp Ser Glu Gln Leu Ser Arg
             20                  25                  30
```

-continued

| GAC | TGT | GAT | GCG | CTA | ATG | GCG | GGC | TGC | ATC | CAG | GAG | GCC | CGT | GAG | CGA | 144 |
| Asp | Cys | Asp | Ala | Leu | Met | Ala | Gly | Cys | Ile | Gln | Glu | Ala | Arg | Glu | Arg | |
| | | 35 | | | | 40 | | | | | 45 | | | | | |

| TGG | AAC | TTC | GAC | TTT | GTC | ACC | GAG | ACA | CCA | CTG | GAG | GGT | GAC | TTC | GCC | 192 |
| Trp | Asn | Phe | Asp | Phe | Val | Thr | Glu | Thr | Pro | Leu | Glu | Gly | Asp | Phe | Ala | |
| | 50 | | | | | 55 | | | | | 60 | | | | | |

| TGG | GAG | CGT | GTG | CGG | GGC | CTT | GGC | CTG | CCC | AAG | CTC | TAC | CTT | CCC | ACG | 240 |
| Trp | Glu | Arg | Val | Arg | Gly | Leu | Gly | Leu | Pro | Lys | Leu | Tyr | Leu | Pro | Thr | |
| 65 | | | | | 70 | | | | | 75 | | | | | 80 | |

| GGG | CCC | CGG | CGA | GGC | CGG | GAT | GAG | TTG | GGA | GGA | GGC | AGG | CGG | CCT | GGC | 288 |
| Gly | Pro | Arg | Arg | Gly | Arg | Asp | Glu | Leu | Gly | Gly | Gly | Arg | Arg | Pro | Gly | |
| | | | | 85 | | | | | 90 | | | | | 95 | | |

| ACC | TCA | CCT | GCT | CTG | CTG | CAG | GGG | ACA | GCA | GAG | GAA | GAC | CAT | GTG | GAC | 336 |
| Thr | Ser | Pro | Ala | Leu | Leu | Gln | Gly | Thr | Ala | Glu | Glu | Asp | His | Val | Asp | |
| | | | 100 | | | | | 105 | | | | | 110 | | | |

| CTG | TCA | CTG | TCT | TGT | ACC | CTT | GTG | CCT | CGC | TCA | GGG | GAG | CAG | GCT | GAA | 384 |
| Leu | Ser | Leu | Ser | Cys | Thr | Leu | Val | Pro | Arg | Ser | Gly | Glu | Gln | Ala | Glu | |
| | | | 115 | | | | | 120 | | | | | 125 | | | |

| GGG | TCC | CCA | GGT | GGA | CCT | GGA | GAC | TCT | CAG | GGT | CGA | AAA | CGG | CGG | CAG | 432 |
| Gly | Ser | Pro | Gly | Gly | Pro | Gly | Asp | Ser | Gln | Gly | Arg | Lys | Arg | Arg | Gln | |
| | 130 | | | | | 135 | | | | | 140 | | | | | |

| ACC | AGC | ATG | ACA | GAT | TTC | TAC | CAC | TCC | AAA | CGC | CGG | CTG | ATC | TTC | TCC | 480 |
| Thr | Ser | Met | Thr | Asp | Phe | Tyr | His | Ser | Lys | Arg | Arg | Leu | Ile | Phe | Ser | |
| 145 | | | | | 150 | | | | | 155 | | | | | 160 | |

| AAG | AGG | AAG | CCC | TAA | | | | | | | | | | | | 495 |
| Lys | Arg | Lys | Pro | | | | | | | | | | | | | |
| | | | 165 | | | | | | | | | | | | | |

( 2 ) INFORMATION FOR SEQ ID NO:2:

( i ) SEQUENCE CHARACTERISTICS:
        ( A ) LENGTH: 164 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

| Met | Ser | Glu | Pro | Ala | Gly | Asp | Val | Arg | Gln | Asn | Pro | Cys | Gly | Ser | Lys |
| 1 | | | | 5 | | | | | 10 | | | | | 15 | |

| Ala | Cys | Arg | Arg | Leu | Phe | Gly | Pro | Val | Asp | Ser | Glu | Gln | Leu | Ser | Arg |
| | | | 20 | | | | | 25 | | | | | 30 | | |

| Asp | Cys | Asp | Ala | Leu | Met | Ala | Gly | Cys | Ile | Gln | Glu | Ala | Arg | Glu | Arg |
| | | 35 | | | | | 40 | | | | | 45 | | | |

| Trp | Asn | Phe | Asp | Phe | Val | Thr | Glu | Thr | Pro | Leu | Glu | Gly | Asp | Phe | Ala |
| | 50 | | | | | 55 | | | | | 60 | | | | |

| Trp | Glu | Arg | Val | Arg | Gly | Leu | Gly | Leu | Pro | Lys | Leu | Tyr | Leu | Pro | Thr |
| 65 | | | | | 70 | | | | | 75 | | | | | 80 |

| Gly | Pro | Arg | Arg | Gly | Arg | Asp | Glu | Leu | Gly | Gly | Gly | Arg | Arg | Pro | Gly |
| | | | | 85 | | | | | 90 | | | | | 95 | |

| Thr | Ser | Pro | Ala | Leu | Leu | Gln | Gly | Thr | Ala | Glu | Glu | Asp | His | Val | Asp |
| | | | 100 | | | | | 105 | | | | | 110 | | |

| Leu | Ser | Leu | Ser | Cys | Thr | Leu | Val | Pro | Arg | Ser | Gly | Glu | Gln | Ala | Glu |
| | | | 115 | | | | | 120 | | | | | 125 | | |

| Gly | Ser | Pro | Gly | Gly | Pro | Gly | Asp | Ser | Gln | Gly | Arg | Lys | Arg | Arg | Gln |
| | 130 | | | | | 135 | | | | | 140 | | | | |

| Thr | Ser | Met | Thr | Asp | Phe | Tyr | His | Ser | Lys | Arg | Arg | Leu | Ile | Phe | Ser |
| 145 | | | | | 150 | | | | | 155 | | | | | 160 |

| Lys | Arg | Lys | Pro |

( 2 ) INFORMATION FOR SEQ ID NO:3:

( i ) SEQUENCE CHARACTERISTICS:
        ( A ) LENGTH: 597 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: Homo sapiens
        ( D ) DEVELOPMENTAL STAGE: Adult
        ( F ) TISSUE TYPE: Kidney     ( v i i ) IMMEDIATE SOURCE:
        ( B ) CLONE: p27kip1

( i x ) FEATURE:
        ( A ) NAME/KEY: CDS
        ( B ) LOCATION: 1..597

( x ) PUBLICATION INFORMATION:
        ( A ) AUTHORS: Polyak, K.
                Lee, Mong-Hong
                Erdjument-Bromage, H.
                Koff, A.
                Roberts, J. M.
                Tempst, P.
                Massague, J.
        ( B ) TITLE: Cloning of p27kip1, a Cyclin-dependent Kinase
               Inhibitor, and a Potential Mediator of
               Extracellular Antimitogenic Signals
        ( C ) JOURNAL: Cell
        ( D ) VOLUME: 78
        ( F ) PAGES: 56-66
        ( G ) DATE: 1994
        ( K ) RELEVANT RESIDUES IN SEQ ID NO:3: FROM 1 TO 597

( x i ) SEQUENCE DESCRIPTION: SEQ ID NO:3:

```
ATG  TCA  AAC  GTG  CGA  GTG  TCT  AAC  GGG  AGC  CCT  AGC  CTG  GAG  CGG  ATG      48
Met  Ser  Asn  Val  Arg  Val  Ser  Asn  Gly  Ser  Pro  Ser  Leu  Glu  Arg  Met
 1              5                        10                       15

GAC  GCC  AGG  CAG  GCG  GAG  CAC  CCC  AAG  CCC  TCG  GCC  TGC  AGG  AAC  CTC      96
Asp  Ala  Arg  Gln  Ala  Glu  His  Pro  Lys  Pro  Ser  Ala  Cys  Arg  Asn  Leu
               20                        25                       30

TTC  GGC  CCG  GTG  GAC  CAC  GAA  GAG  TTA  ACC  CGG  GAC  TTG  GAG  AAG  CAC     144
Phe  Gly  Pro  Val  Asp  His  Glu  Glu  Leu  Thr  Arg  Asp  Leu  Glu  Lys  His
          35                        40                       45

TGC  AGA  GAC  ATG  GAA  GAG  GCG  AGC  CAG  CGC  AAG  TGG  AAT  TTC  GAT  TTT     192
Cys  Arg  Asp  Met  Glu  Glu  Ala  Ser  Gln  Arg  Lys  Trp  Asn  Phe  Asp  Phe
     50                        55                       60

CAG  AAT  CAC  AAA  CCC  CTA  GAG  GGC  AAG  TAC  GAG  TGG  CAA  GAG  GTG  GAG     240
Gln  Asn  His  Lys  Pro  Leu  Glu  Gly  Lys  Tyr  Glu  Trp  Gln  Glu  Val  Glu
65                       70                       75                       80

AAG  GGC  AGC  TTG  CCC  GAG  TTC  TAC  TAC  AGA  CCC  CCG  CGG  CCC  CCC  AAA     288
Lys  Gly  Ser  Leu  Pro  Glu  Phe  Tyr  Tyr  Arg  Pro  Pro  Arg  Pro  Pro  Lys
                    85                       90                       95

GGT  GCC  TGC  AAG  GTG  CCG  GCG  CAG  GAG  AGC  CAG  GAT  GTC  AGC  GGG  AGC     336
Gly  Ala  Cys  Lys  Val  Pro  Ala  Gln  Glu  Ser  Gln  Asp  Val  Ser  Gly  Ser
               100                      105                      110

CGC  CCG  GCG  GCG  CCT  TTA  ATT  GGG  GCT  CCG  GCT  AAC  TCT  GAG  GAC  ACG     384
Arg  Pro  Ala  Ala  Pro  Leu  Ile  Gly  Ala  Pro  Ala  Asn  Ser  Glu  Asp  Thr
          115                      120                      125

CAT  TTG  GTG  GAC  CCA  AAG  ACT  GAT  CCG  TCG  GAC  AGC  CAG  ACG  GGG  TTA     432
His  Leu  Val  Asp  Pro  Lys  Thr  Asp  Pro  Ser  Asp  Ser  Gln  Thr  Gly  Leu
     130                     135                      140

GCG  GAG  CAA  TGC  GCA  GGA  ATA  AGG  AAG  CGA  CCT  GCA  ACC  GAC  GAT  TCT     480
```

|     |     |     |     |     |     |     |     |     |     |     |     |     |     |     |     |
|-----|-----|-----|-----|-----|-----|-----|-----|-----|-----|-----|-----|-----|-----|-----|-----|
| Ala | Glu | Gln | Cys | Ala | Gly | Ile | Arg | Lys | Arg | Pro | Ala | Thr | Asp | Asp | Ser |
| 145 |     |     |     |     | 150 |     |     |     |     | 155 |     |     |     |     | 160 |

| TCT | ACT | CAA | AAC | AAA | AGA | GCC | AAC | AGA | ACA | GAA | GAA | AAT | GTT | TCA | GAC | 528 |
|-----|-----|-----|-----|-----|-----|-----|-----|-----|-----|-----|-----|-----|-----|-----|-----|-----|
| Ser | Thr | Gln | Asn | Lys | Arg | Ala | Asn | Arg | Thr | Glu | Glu | Asn | Val | Ser | Asp |     |
|     |     |     |     | 165 |     |     |     |     | 170 |     |     |     |     | 175 |     |     |

| GGT | TCC | CCA | AAT | GCC | GGT | TCT | GTG | GAG | CAG | ACG | CCC | AAG | AAG | CCT | GGC | 576 |
|-----|-----|-----|-----|-----|-----|-----|-----|-----|-----|-----|-----|-----|-----|-----|-----|-----|
| Gly | Ser | Pro | Asn | Ala | Gly | Ser | Val | Glu | Gln | Thr | Pro | Lys | Lys | Pro | Gly |     |
|     |     |     | 180 |     |     |     |     | 185 |     |     |     |     | 190 |     |     |     |

| CTC | AGA | AGA | CGT | CAA | ACG | TAA | 597 |
|-----|-----|-----|-----|-----|-----|-----|-----|
| Leu | Arg | Arg | Arg | Gln | Thr |     |     |
|     |     | 195 |     |     |     |     |     |

( 2 ) INFORMATION FOR SEQ ID NO:4:

( i ) SEQUENCE CHARACTERISTICS:
        ( A ) LENGTH: 198 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:4:

| Met | Ser | Asn | Val | Arg | Val | Ser | Asn | Gly | Ser | Pro | Ser | Leu | Glu | Arg | Met |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Ala | Arg | Gln | Ala | Glu | His | Pro | Lys | Pro | Ser | Ala | Cys | Arg | Asn | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Phe | Gly | Pro | Val | Asp | His | Glu | Glu | Leu | Thr | Arg | Asp | Leu | Glu | Lys | His |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Cys | Arg | Asp | Met | Glu | Glu | Ala | Ser | Gln | Arg | Lys | Trp | Asn | Phe | Asp | Phe |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gln | Asn | His | Lys | Pro | Leu | Glu | Gly | Lys | Tyr | Glu | Trp | Gln | Glu | Val | Glu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Lys | Gly | Ser | Leu | Pro | Glu | Phe | Tyr | Tyr | Arg | Pro | Pro | Arg | Pro | Pro | Lys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Gly | Ala | Cys | Lys | Val | Pro | Ala | Gln | Glu | Ser | Gln | Asp | Val | Ser | Gly | Ser |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Arg | Pro | Ala | Ala | Pro | Leu | Ile | Gly | Ala | Pro | Ala | Asn | Ser | Glu | Asp | Thr |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| His | Leu | Val | Asp | Pro | Lys | Thr | Asp | Pro | Ser | Asp | Ser | Gln | Thr | Gly | Leu |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ala | Glu | Gln | Cys | Ala | Gly | Ile | Arg | Lys | Arg | Pro | Ala | Thr | Asp | Asp | Ser |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Ser | Thr | Gln | Asn | Lys | Arg | Ala | Asn | Arg | Thr | Glu | Glu | Asn | Val | Ser | Asp |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Gly | Ser | Pro | Asn | Ala | Gly | Ser | Val | Glu | Gln | Thr | Pro | Lys | Lys | Pro | Gly |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Leu | Arg | Arg | Arg | Gln | Thr |
|-----|-----|-----|-----|-----|-----|
|     |     | 195 |     |     |     |

( 2 ) INFORMATION FOR SEQ ID NO:5:

( i ) SEQUENCE CHARACTERISTICS:
        ( A ) LENGTH: 297 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Human papillomavirus
        ( B ) STRAIN: HPV-16

(vii) IMMEDIATE SOURCE:
    (B) CLONE: E7

(ix) FEATURE:
    (A) NAME/KEY: CDS
    (B) LOCATION: 1..297

(xi) SEQUENCE DESCRIPTION: SEQ ID NO:5:

| ATG | CAT | GGA | GAT | ACA | CCT | ACA | TTG | CAT | GAA | TAT | ATG | TTA | GAT | TTG | CAA | 48 |
| Met | His | Gly | Asp | Thr | Pro | Thr | Leu | His | Glu | Tyr | Met | Leu | Asp | Leu | Gln | |
| 1 | | | | 5 | | | | | 10 | | | | | 15 | | |

| CCA | GAG | ACA | ACT | GAT | CTC | TAC | TGT | TAT | GAG | CAA | TTA | AAT | GAC | AGC | TCA | 96 |
| Pro | Glu | Thr | Thr | Asp | Leu | Tyr | Cys | Tyr | Glu | Gln | Leu | Asn | Asp | Ser | Ser | |
| | | | 20 | | | | | 25 | | | | | 30 | | | |

| GAG | GAG | GAG | GAT | GAA | ATA | GAT | GGT | CCA | GCT | GGA | CAA | GCA | GAA | CCG | GAC | 144 |
| Glu | Glu | Glu | Asp | Glu | Ile | Asp | Gly | Pro | Ala | Gly | Gln | Ala | Glu | Pro | Asp | |
| | | 35 | | | | | 40 | | | | | 45 | | | | |

| AGA | GCC | CAT | TAC | AAT | ATT | GTA | ACC | TTT | TGT | TGC | AAG | TGT | GAC | TCT | ACG | 192 |
| Arg | Ala | His | Tyr | Asn | Ile | Val | Thr | Phe | Cys | Cys | Lys | Cys | Asp | Ser | Thr | |
| | 50 | | | | | 55 | | | | | 60 | | | | | |

| CTT | CGG | TTG | TGC | GTA | CAA | AGC | ACA | CAC | GTA | GAC | ATT | CGT | ACT | TTG | GAA | 240 |
| Leu | Arg | Leu | Cys | Val | Gln | Ser | Thr | His | Val | Asp | Ile | Arg | Thr | Leu | Glu | |
| 65 | | | | | 70 | | | | | 75 | | | | | 80 | |

| GAC | CTG | TTA | ATG | GGC | ACA | CTA | GGA | ATT | GTG | TGC | CCC | ATC | TGT | TCT | CAG | 288 |
| Asp | Leu | Leu | Met | Gly | Thr | Leu | Gly | Ile | Val | Cys | Pro | Ile | Cys | Ser | Gln | |
| | | | | 85 | | | | | 90 | | | | | 95 | | |

| AAA | CCA | TAA | | | | | | | | | | | | | | 297 |
| Lys | Pro | | | | | | | | | | | | | | | |

(2) INFORMATION FOR SEQ ID NO:6:

(i) SEQUENCE CHARACTERISTICS:
        (A) LENGTH: 98 amino acids
        (B) TYPE: amino acid
        (D) TOPOLOGY: linear (ii) MOLECULE TYPE: protein (xi) SEQUENCE DESCRIPTION: SEQ ID NO:6:

| Met | His | Gly | Asp | Thr | Pro | Thr | Leu | His | Glu | Tyr | Met | Leu | Asp | Leu | Gln |
| 1 | | | | 5 | | | | | 10 | | | | | 15 | |

| Pro | Glu | Thr | Thr | Asp | Leu | Tyr | Cys | Tyr | Glu | Gln | Leu | Asn | Asp | Ser | Ser |
| | | | 20 | | | | | 25 | | | | | 30 | | |

| Glu | Glu | Glu | Asp | Glu | Ile | Asp | Gly | Pro | Ala | Gly | Gln | Ala | Glu | Pro | Asp |
| | | 35 | | | | | 40 | | | | | 45 | | | |

| Arg | Ala | His | Tyr | Asn | Ile | Val | Thr | Phe | Cys | Cys | Lys | Cys | Asp | Ser | Thr |
| | 50 | | | | | 55 | | | | | 60 | | | | |

| Leu | Arg | Leu | Cys | Val | Gln | Ser | Thr | His | Val | Asp | Ile | Arg | Thr | Leu | Glu |
| 65 | | | | | 70 | | | | | 75 | | | | | 80 |

| Asp | Leu | Leu | Met | Gly | Thr | Leu | Gly | Ile | Val | Cys | Pro | Ile | Cys | Ser | Gln |
| | | | | 85 | | | | | 90 | | | | | 95 | |

| Lys | Pro |

METHOD AND KIT FOR EVALUATING HUMAN PAPILLOMAVIRUS TRANSFORMED CELLS

The present invention relates to the identification of compounds capable of inhibiting dysregulated cellular proliferation and/or differentiation caused by human papillomaviruses. The invention also relates to the field of characterizing proliferation of transformed cells, and more specifically, detection of proliferating cells transformed by human papillomaviruses.

BACKGROUND OF THE INVENTION

Human papillomaviruses (HPVs) are small DNA viruses of the papovavirus family that infect human epithelial cells. About sixty genetically distinct strains of HPV have been identified to date, many of which appear to be responsible for different disease states. For example, "low-risk" HPVs, e.g., HPV-6 and HPV-11 cause benign hyperplasias such as genital warts, while "high-risk" HPVs, e.g., HPV-16 and HPV-18 can cause carcinomas such as cervical or penile carcinoma. On infection of a cell, the genomes of the HPVs are episomal, the low-risk HPV strains remaining so and the high-risk HPV integrating into the cellular genome in the course of pathogenesis. Two HPV encoded proteins, E6 and E7, are consistently expressed in the cancers and lead to transformation, or loss of control of growth, of infected cells. HPV E6 and E7 are thus commonly termed "oncoproteins".

The transforming functions of the papillomaviruses reflect their ability to interfere with control mechanisms that govern the normal program of cell growth and differentiation. Since the HPVs do not encode their own DNA replication machinery, they must exploit the host cell's replication apparatus in order to establish and maintain viral DNA replication in the infected tissue. Most of the skin cells that papillomaviruses infect have withdrawn from the cell replication cycle, having undergone an intricate program of terminal differentiation. Thus, in order to replicate viral DNA in such inactive cells, papillomaviruses subvert key regulatory mechanisms that govern cellular division and differentiation. For example, the HPV E6 oncoprotein interacts with the nuclear phosphoprotein p53 which is believed to act as a minor suppressor in its native state by functioning as a key mediator of DNA repair. The HPV E7 oncoprotein is known to interact with the "pocket proteins", a class of cellular proteins that include the retinoblastoma tumor suppressor protein pRB, p107, and p130.

The p53 and RB tumor suppressors are believed to act by imposing specific blocks to the progression of the cell cycle. If DNA damage occurs in a normal cell, wild type p53 levels increase. By virtue of its ability to bind to DNA in a sequence-specific manner, p53 stimulates expression of a number of genes, for example, the gene encoding a 21 kD protein variously known as p21, WAF1, SDI1, PIC1 and CIP1 (hereinafter referred to as p21$^{CIP1}$). The nucleotide and amino acid sequences of p21$^{CIP1}$ are set forth in SEQ ID NO:1 and SEQ ID NO:2. The p21$^{CIP1}$ protein suppresses growth by inhibiting the activities of a class of protein kinases, the cyclin dependent kinases (cdks), which affect the temporal progression of the cell cycle. In their native state, the cdks form complexes with a regulatory subunit (a cyclin). A large number of cyclins have been identified, as have the specific cdks with which they associate. See, for example, PCT/US/00961 and T. Hunter et al., Cell 79, 573–582 (1994), incorporated herein by reference. When the cyclin/cdk complexes are inhibited by p21$^{CIP1}$, cell division is blocked at an important checkpoint in the late G1 phase early in the cell replication cycle. When p21$^{CIP1}$ does not inhibit the cyclin/cdk complexes, they stimulate cells to proceed through the cell cycle by phosphorylating and thus modulating the activity of the RB tumor suppressor as well as other regulatory proteins.

As set forth above, the HPV E7 oncoprotein also interacts with the RB tumor suppressor; however, the nature of the interaction differs from that of the cyclin/cdk complexes with RB. Hypophosphorylated RB suppresses transcription by complexing with the transcription factor E2F, and upon phosphorylation by the cyclin/cdk complexes, RB releases E2F, thus increasing transcription of genes needed for cellular replication. When HPV E7 binds to RB, E2F is also released.

Because of the prevalence of HPV infection, a need remains for additional diagnostic methods and therapeutic compounds. A need also exists for determining the potential for a pre-malignant high-risk HPV infection to progress to a malignant state.

SUMMARY OF THE INVENTION

The present inventors have for the first time discovered that the HPV E7 oncoprotein interacts with p21$^{CIP1}$ and overcomes p21$^{CIP1}$ inhibition of the kinase activity of cyclin/cdk complexes. In accordance with the invention, therefore, methods for identifying potential anti-carcinoma compounds, methods for inhibiting growth of HPV-infected cells, methods for determining the proliferative state of a transformed cell, and kits for diagnosing the proliferative state of HPV-infected cells are described.

In one embodiment, the invention provides a method of identifying a compound that inhibits the ability of human papillomavirus oncoprotein E7 to stimulate proliferation of human papillomavirus-infected cells, comprising the steps of:

(a) isolating cyclin/cyclin dependent kinase complexes from the cells;

(b) dividing the cyclin/cyclin dependent kinase complexes into a plurality of aliquots;

(c) adding human papillomavirus oncoprotein E7 and a cyclin-dependent kinase inhibitor to at least two aliquots;

(d) adding a test compound to one of the aliquots of step (c) ;

(e) measuring the kinase activity of the respective aliquots;

(f) detecting differences in the measured kinase activities of the respective aliquots wherein a lesser kinase activity in the aliquot including the test compound compared to other aliquots is indicative of said test compound being a compound that inhibits the ability of human papillomavirus oncoprotein E7 to stimulate proliferation of the human papillomavirus-infected cells.

In another embodiment, the invention provides a method of inhibiting growth of a human papillomavirus-infected cell comprising administering to the cell a therapeutically effective mount of a compound that interferes with the ability of human papillomavirus oncoprotein E7 to interact with a cyclin-dependent kinase inhibitor.

In another embodiment, the invention provides a kit for diagnosing the proliferative state of a population of cells infected with a human papillomavirus, which comprises:

(a) a cyclin-dependent kinase inhibitor;

(b) a dephosphorylated phosphoprotein; and (c) a compound capable of donating a labeled molecule to a phosphate accepting site on the dephosphorylated phosphoprotein, said compound being selected from the group consisting of a labeled phosphate and a labeled phosphate analog.

In another embodiment, the invention provides a kit for diagnosing the proliferative state of a population of transformed cells, which comprises:

(a) a human papillomavirus E7 oncoprotein;

(b) a dephosphorylated phosphoprotein; and (c) a compound capable of donating a labeled molecule to a phosphate accepting site on the dephosphorylated phosphoprotein, said compound being selected from the group consisting of a labeled phosphate and a labeled phosphate analog.

In yet another embodiment, the invention provides a method of evaluating the proliferative state of a transformed cell which comprises:

a. isolating cyclin/cyclin-dependent kinase complexes from the cell, and dividing said complexes into a plurality of aliquots;

b. adding human papilloma virus E7 oncoprotein to at least one aliquot from step a;

c. isolating an untransformed cell which is substantially homogeneic with the transformed cell;

d. isolating cyclin/cyclin-dependent kinase complexes from the untransformed cell of step c, and dividing said complexes into a plurality of aliquots;

e. adding papilloma virus E7 oncoprotein to at least one aliquot from step d; and f. measuring the kinase activities of the respective aliquots, wherein a proliferating transformed cell is characterized by a greater kinase activity in comparison to the kinase activity of the substantially homogeneic untransformed cell.

BRIEF DESCRIPTION OF THE DRAWINGS

The foregoing and other objects of the invention, the various features thereof, as well as the invention itself, may be more fully understood from the following description, when read together with the accompanying drawings in which.

DETAILED DESCRIPTION OF THE PREFERRED EMBODIMENTS

Figure 1:
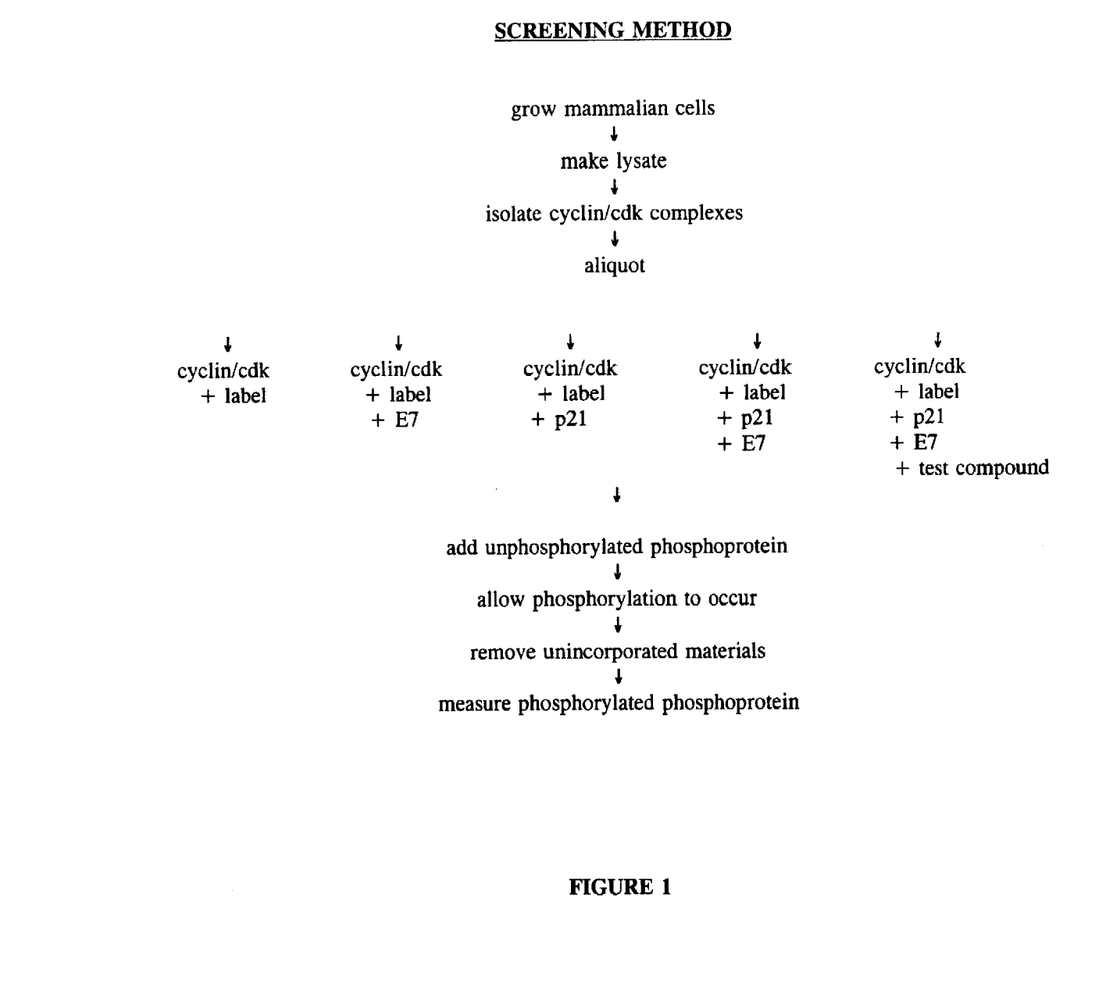
FIG. 1 sets forth a flow diagram of the invention as embodied in a method for identifying potential anti-carcinoma compounds.
Figure 2:
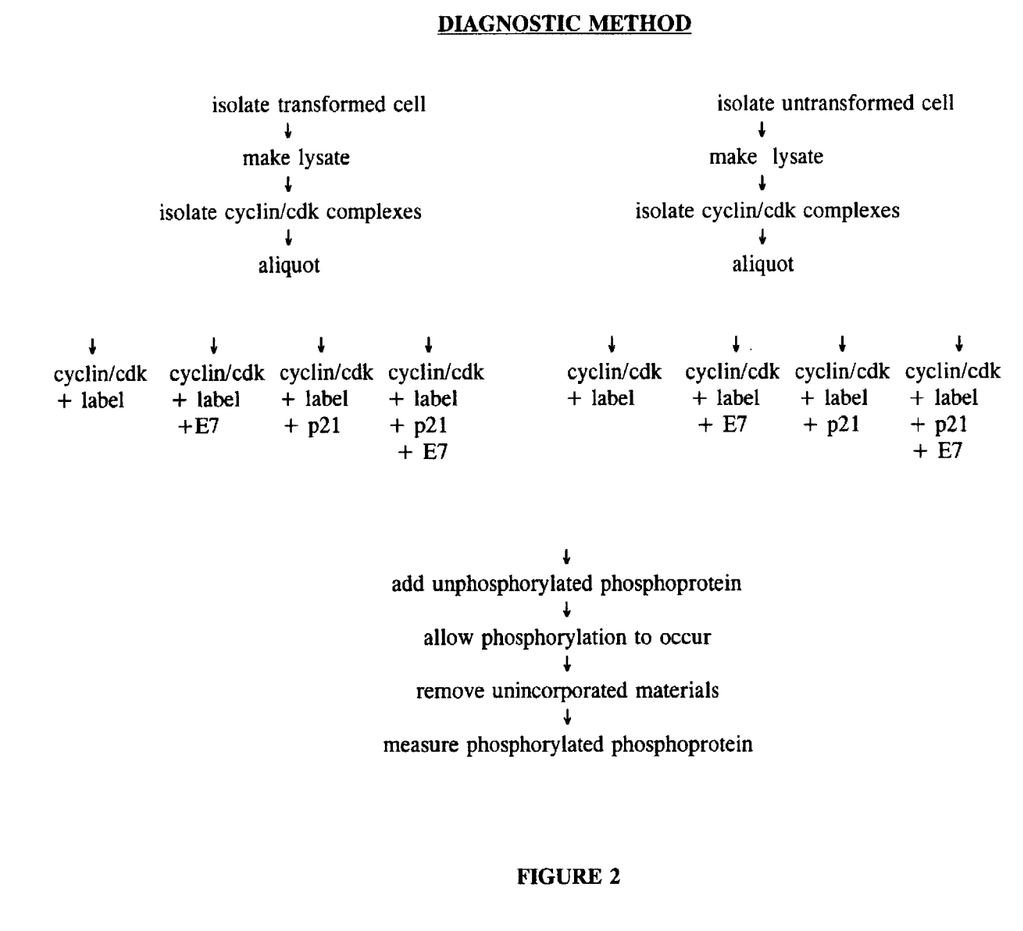
FIG. 2 sets forth a flow diagram of the diagnostic method of the invention.

In accordance with the invention, an inhibitor of the kinase activity of cyclin/cyclin dependent kinase complexes and the HPV E7 oncoprotein are used in methods for identifying potential anti-carcinoma or anti-viral compounds and for diagnosing the proliferative states of transformed cells. As defined in the present invention, an inhibitor of the kinase activity of cyclin/cyclin dependent kinase complexes comprises any of a family of small cyclin-dependent kinase inhibitors known as CDIs which are capable of interacting with HPV E7. For example, the $p21^{CIP1}$ protein having the amino acid sequence set forth in SEQ ID NO:1 and SEQ ID NO:2 or the $p27^{KIP1}$ protein having the amino acid sequence set forth in SEQ ID NO:3 and SEQ ID NO:4 may be used in the methods of the invention.

The basic method of the invention may be performed as follows. Cyclin/cyclin dependent kinase complexes are isolated from mammalian cells, for example, by making an extract or lysate of the cells. Any mammalian cell may be used as a source of cyclin/cyclin dependent kinase complexes. For example, any of the mammalian cells described below in relation to recombinant expression of proteins may also be used as a source of cyclin/cyclin dependent kinase complexes. In addition, other cells may be used to prepare cyclin/cyclin dependent kinase complexes; for example, any transformed cell line may be used, as well as normal diploid cells, cell strains derived from in vitro culture of primary tissue, primary explants (especially from tumors), and the like, may act as a source for cyclin/cyclin dependent kinase complexes. The mammalian cells are grown in tissue culture using known methods; for example, the cells may be grown in monolayer culture or in liquid culture using a known nutrient solution supplemented with fetal calf serum and antibiotics. Preferably Dulbecco's Modified Essential Medium containing 10% fetal calf serum, streptomycin (50 µg/ml) and penicillin (50 units/ml) is used to grow the cells. The cells are grown until they are 50 to 80% confluent.

Any method for making a cell extract may be used, for example, by lysis with a detergent such as Nonidet P-40 (NP-40), Triton-X-100, and the like, in a suitable buffer. Preferably, a lysis buffer containing 0.1% NP-40, 100 mM trishydroxymethylaminomethane pH 7.4, and 120 mM NaCl is used. Alternatively a cell lysate may be obtained by other methods well known in the art, for example, using sonication, osmotic shock, or mechanical rupture. Nuclear extracts prepared according to standard procedures may also be used to prepare cyclin/cyclin-dependent kinase complexes for use in the method of the invention. Protease inhibitors such as phenylmethylsulfonyl fluoride, aprotinin, leupeptin, and the like are included in the lysis buffer prior to further processing. After lysis, the lysate is centrifuged to remove cellular debris and the supernatant containing the cyclin/cyclin dependent kinase complexes is retained. This supernatant may be quick frozen and stored at ultralow temperatures (i.e., at about −80° C.) prior to use, or it may be subjected to further processing without freezing.

Cyclin/cyclin dependent kinase complexes are isolated from the supernatant using any suitable method, for example immunoprecipitation, affinity chromatography, preparative gel electrophoresis, and the like. Alternatively, the cyclin/cyclin dependent kinase complexes may be in the form of reconstituted complexes derived from recombinant expression of the DNA sequences encoding the respective proteins. Methods for expressing DNA sequences to obtain recombinant proteins are generally described below. Methods for co-expressing proteins are known. Preferably the cyclin/cyclin dependent kinase complexes are isolated using immunoprecipitation. More preferably, the cyclin/cyclin dependent kinase complexes are immunoprecipitated using a monoclonal antibody specific for a cyclin or for its specifically associated cyclin dependent kinase. Cyclin/cyclin dependent kinase complexes isolated in this way are precipitated using a secondary reagent such as protein A, protein G, sepharose-conjugated protein A or protein G, or a suitable second antibody. Most preferably, a monoclonal antibody specific for a cyclin or for its specifically associated cyclin dependent kinase, which is conjugated to a carrier resin such as agarose or sepharose, is used to immunoprecipitate the cyclin/cyclin dependent kinase complexes used in the method of the invention. Monoclonal antibodies specific for cyclins are known and are commercially available: for example, a monoclonal antibody specific for cyclin A which is conjugated to agarose beads is available from Santa Cruz Biotechnology (catalog number sc-239 AC). Commercially available monoclonal antibodies specific for other cyclins or cyclin-dependent kinases are identified in Linscott's Directory of Immunological & Biological Reagents (4877 Grange Road, Santa Rosa, Calif. 95404). Alternatively, purified cyclins or cyclin-dependent kinases may act as immunogens to produce monoclonal antibodies using known methods, such as those described in *Antibodies, A Laboratory Manual*, E. Harlow and D. Lane, Cold Spring Harbor Laboratory Press (1988).

The isolated cyclin/cyclin-dependent kinase complexes are washed to remove substances which could produce artifacts. Any suitable buffer which maintains the conformation of the cyclin/cyclin-dependent kinase complex may be used to perform this washing. Preferably, the lysis buffer described above is used to wash the complexes. A buffer suitable for performance of kinase assays is then used to wash the cyclin/cyclin-dependent kinase complexes further, thereby equilibrating the complexes for the remaining steps of the method. Any buffer suitable for performing kinase assays may be used for this washing/equilibration step. Preferably, a buffer comprised of 50 mM trishydroxymethylaminomethane, pH 7.4, and 20 mM $MgCl_2$ is used to wash and equilibrate the cyclin/cyclin-dependent kinase complexes.

After the isolated cyclin/cyclin-dependent kinase complexes are washed and equilibrated, they are resuspended in a kinase buffer and aliquotted. Preferably, the kinase buffer contains 50 mM trishydroxymethylaminomethane, pH 7.4, 20 mM $MgCl_2$, 1 mM dithiothreitol, and, optionally, 100 µM unlabeled adenosine triphosphate. The CDI and HPV E7 proteins are then added to each aliquot and allowed to interact on ice for a suitable time, preferably about ten minutes. Appropriate controls are performed in parallel aliquots. A dephosphorylated phosphoprotein and a compound capable of donating a labeled molecule to a phosphate accepting site on the phosphoprotein are then added to each aliquot, and a kinase reaction is allowed to proceed at a suitable temperature and for a suitable time, both of which may be determined using known methods of chemical kinetics analysis. The kinase reaction is quenched using a buffer containing a suitable quenching agent such as sodium dodecyl sulfate, and the relative amounts of phosphorylated phosphoprotein are measured and compared.

Any form of the CDI protein may be used in the methods of the invention, so long as the CDI protein maintains its ability to inhibit the kinase activity and to interact with an HPV E7 oncoprotein. For example, the CDI protein may be in the form of a recombinantly expressed protein, which may optionally be fused to a carrier molecule such as glutathione-S-transferase. Fragments of the CDI protein which retain the ability to interact with and inactivate cyclin/cyclin-dependent kinase complexes may also be employed in the method of the invention.

Similarly, any form of HPV E7 oncoprotein may be used in the methods of the invention, so long as the HPV E7 oncoprotein maintains its ability to interact with and/or inactivate the cyclin/cyclin-dependent kinase inhibitor protein used in the method. For example, the HPV-16 E7 oncoprotein having the amino acid sequence set forth in SEQ ID NO:5 and SEQ ID NO:6 may be used in the methods of the invention, or fragments of the HPV E7 oncoprotein which retain the ability to interact with and/or inactivate the cyclin/cyclin-dependent kinase inhibitor protein used in the method may be employed in the method of the invention. The HPV E7 oncoprotein may be used in the form of a recombinantly expressed protein, which may optionally be fused to a carrier molecule such as glutathione-S-transferase.

When the proteins used in the methods of the invention are recombinantly expressed, DNAs encoding the proteins such as those set forth in SEQ ID NO:1, SEQ ID NO:3, and SEQ ID NO:5 are operably linked to an expression control sequence. As defined herein, "operably linked" means enzymatically or chemically ligated to form a covalent bond between the DNA encoding the protein and the expression control sequence, said ligation being effected in such a way that the protein is expressed by a host cell which has been transformed (transfected) with the ligated DNA/expression control sequence. Many suitable expression control sequences are known in the art, for example, general methods of expressing recombinant proteins in mammalian cells are also known and are exemplified in R. Kaufman, *Methods in Enzymology* 185, 537–566 (1990). Many DNA vectors for expression of proteins in mammalian cells are known, for example, the pcDNA3 or the pRc/RSV vectors available from Invitrogen, San Diego, Calif. U.S.A.

A number of types of mammalian cells may act as suitable host cells for expression of the proteins used in the methods of the invention. For example, suitable mammalian host cells include, monkey COS cells, Chinese Hamster Ovary (CHO) cells, human kidney 293 cells, human epidermal A431 cells, human Colo205 cells, mouse 3T3 cells, CV-1 cells, other transformed primate cell lines, HeLa cells, mouse L cells, baby hamster kidney (BHK) cells, HL-60 cells, U937 cells, hamster kidney (HaK) cells, or the like.

Alternatively, the proteins used in the methods of the invention may be recombinantly produced by operably linking the DNAs which encode them to suitable control sequences in one or more insect expression vectors, and employing an insect expression system. Materials and methods for baculovirus/insect cell expression systems are commercially available in kit form from, e.g., Invitrogen, San Diego, Calif. U.S.A. (the MacBac® kit) or PharMingen, San Diego, Calif. U.S.A. (the BaculoGold™ Transfection Kit). Such methods are well known in the art, as described in Summers and Smith, *Texas Agricultural Experiment Station Bulletin No. 1555* (1987), incorporated herein by reference.

The proteins used in the present invention may also be produced in lower eukaryotes such as yeast or in prokaryotes such as bacteria. When expressed in yeast, the DNAs encoding the proteins used in the methods of the invention are operably linked to an expression control sequence suitable for expression in yeast. Many vectors for expression of heterologous proteins in yeast are known, for example, the pYES2 vector available from Invitrogen, San Diego, Calif. U.S.A. Potentially suitable yeast host cell strains include *Saccharomyces cerevisiae*, *Schizosaccharomyces pombe*, Kluyveromyces strains, Candida, or any yeast strain capable of expressing heterologous proteins. When expressed in bacteria, the DNAs encoding the proteins used in the methods of the invention are operably linked to an expression control sequence suitable for expression in bacteria. Many vectors for expression of heterologous proteins in bacteria are known. Potentially suitable bacterial host cells include *Escherichia coli*, *Bacillus subtilis*, attenuated strains of *Salmonella typhimurium*, and the like. When expressed in bacteria, the proteins used in the method of the invention may be initially obtained in inclusion bodies and may be refolded using known methods and chaotropic agents. Bacterially expressed proteins for use in the invention may also be obtained in the form of fusion proteins, for example, as glutathione-S-transferase or β-galactosidase fusion proteins, using methods which are well known in the art, for example, using the pGEX vectors available from Pharmacia, Piscataway, N.J., U.S.A.

Any dephosphorylated phosphoprotein may be used to measure the kinase activity of the cyclin/cyclin dependent kinase complexes in accordance with the method of the invention. For example, dephosphorylated histones may be used as substrates for the cyclin/cyclin dependent kinase complexes, in performing the method of the invention. Casein (e.g., cat. #c-4032, Sigma, St. Louis, Mo. U.S.A.) may also be used as a substrate for the cyclin/cyclin dependent kinase complexes in accordance with the invention. Preferably, historic H1 is used to perform the method of the invention. Historic H1 suitable for use in the method of the invention is commercially available from Boehringer-Mannheim, Indianapolis, Ind., U.S.A. (cat. #223–549).

Any compound capable of donating a labeled molecule to a phosphate accepting site on the phosphoprotein and that can serve as a substrate for the kinase may be used to perform the kinase assay used in the method of the invention. For example, a labeled phosphate compound or a labeled phosphate analog compound may be used in the kinase assay in accordance with the present invention. Preferably, a labeled nucleoside triphosphate, in particular, a labeled adenosine triphosphate may be used to donate the labeled phosphate to the dephosphorylated phosphoprotein. Alternatively a labeled nucleoside triphosphate analog such as a labeled nucleoside phosphorothioate may be used to donate a labeled sulfate to the dephosphorylated phosphoprotein. The label on the phosphate or phosphate analog compound will preferably occur at the γ-position of the phosphate or phosphorothioate moiety of the donating compound. Any kind of label may be used to perform the method of the invention. Preferably, a chemiluminescent label is used to label the γ-position of the phosphate or phosphorothioate moiety of the donating compound. More preferably, a radioactive label is used to label the γ-position of the phosphate or phosphorothioate moiety of the donating compound. Any radioactive label may be used, however, $^{32}$P, $^{33}$P, or $^{35}$S are preferable as labels in the γ-position of the phosphate or phosphorothioate moiety of the donating compound.

When the method of the invention is used to identify a compound that inhibits the ability of HPV E7 oncoprotein to stimulate proliferation of a population of infected cells, mammalian cells infected with HPV are used to prepare the cyclin/cyclin-dependent kinase complexes. Alternatively, mammalian cells containing the HPV E6 and/or E7 oncogenes are used to prepare the cyclin/cyclin-dependent kinase complexes. Any HPV-infected mammalian cell may be used in this embodiment of the invention, for example, any of the mammalian cells identified above may be used. Preferably, a transformed cell line derived from a cervical or penile carcinoma is used to perform this embodiment of the method of the invention. Many such cell lines are known, for example, HeLa cells, SiHa, CaSki, C4-I, and the like.

In accordance with this embodiment, a test compound is added to at least one aliquot of the isolated cyclin/cyclin-dependent kinase complexes in kinase buffer. Of course, a plurality of test compounds may be tested at one time using multiwell microtiter plates or any other apparatus suitable for assaying multiple samples. The method of identifying a compound that inhibits the ability of HPV E7 oncoprotein to stimulate proliferation of a population of infected cells may be robotized in accordance with the present invention.

The kinase activities of the cyclin/cyclin-dependent kinase complexes in the presence of the test compound are measured and compared to those of control aliquots which do not contain the test compound. In accordance with the invention, a test compound having a kinase activity which is less than that of the control aliquot is considered to be capable of inhibiting the ability of HPV oncoprotein E7 to stimulate proliferation of the HPV-infected cell. Compounds found to reduce the control aliqout's kinase activity by at least 10%, preferably greater than about 50% or more of the control aliquot's kinase activity may thus be identified and then secondarily screened in other proliferation assays, including growth suppression in HPV-positive cells such as HeLa cells, CaSki cells, SiHa cells, C4-I cells, and the like. By these means compounds having inhibitory activity for HPV oncoprotein E7-mediated stimulation of proliferation of HPV-infected cells may be identified.

The present invention is also embodied as a kit for determining or diagnosing the proliferative state of a population of cells infected with a human papillomavirus or for determining or diagnosing the proliferative state of a population of transformed cells. The kit for determining or diagnosing the proliferative state of a population of cells infected with a human papillomavirus comprises a CDI protein, a dephosphorylated phosphoprotein, and a compound capable of donating a labeled molecule to a phosphate accepting site on the dephosphorylated phosphoprotein, said compound being selected from the group consisting of a labeled phosphate and a labeled phosphate analog. Any form of the CDI protein may be included in the kit of the invention, so long as the CDI protein maintains its ability to inhibit the kinase activity and to interact with and/or to be inactivated by an HPV E7 oncoprotein. For example, the CDI protein may be in the form of a recombinantly expressed protein, which may optionally be fused to a carrier molecule such as glutathione-S-transferase or β-galactosidase. Fragments of the CDI protein which retain the ability to interact with and/or inactivate cyclin/cyclin-dependent kinase complexes may also be included in the kit of the invention.

The kit for determining or diagnosing the proliferative state of a population of transformed cells comprises an HPV E7 oncoprotein, a dephosphorylated phosphoprotein, and a compound capable of donating a labeled molecule to a phosphate accepting site on the dephosphorylated phosphoprotein, said compound being selected from the group consisting of a labeled phosphate and a labeled phosphate analog. Any form of the HPV E7 oncoprotein may be included in the kit of the invention, so long as the HPV E7 ontoprotein maintains its ability to inhibit the kinase activity and/or to interact with a CDI within the transformed cell. For example, the HPV E7 oncoprotein may be in the form of a recombinantly expressed protein, which may optionally be fused to a carrier molecule such as glutathione-S-transferase or β-galactosidase. Fragments of the HPV E7 oncoprotein which retain the ability to interact with and/or activate cyclindcyclin-dependent kinase complexes may also be included in the kit of the invention.

Any dephosphorylated phosphoprotein may be included in the kit of the invention. Preferably, a histone or casein is included in the kit of the invention. Histone H 1 is especially preferred for inclusion in the kit of the invention. Any compound capable of donating a labeled molecule to a phosphate accepting site on the phosphoprotein may be included in the kit of the invention. For example, a labeled phosphate compound or a labeled phosphate analog compound may be included in the kit of the present invention. Preferably, a labeled nucleoside triphosphate, in particular, a labeled adenosine triphosphate may be included in the kit of the invention to donate the labeled phosphate to the dephosphorylated phosphoprotein. Alternatively a labeled nucleoside triphosphate analog such as a labeled nucleoside phosphorothioate may be included in the kit. The label on the phosphate or phosphate analog compound will preferably occur at the γ-position of the phosphate or phosphorothioate moiety of the donating compound. Any kind of label may be included in the kit of the invention. Preferably, a chemiluminescent label is used to label the γ-position of the phosphate or phosphorothioate moiety of the donating compound. More preferably, a radioactive label is used to label the γ-position of the phosphate or phosphorothioate moiety of the donating compound. Any radioactive label may be used, however, $^{32}$p, $^{33}$p, or $^{35}$S are preferable as labels in the γ-position of the phosphate or phosphorothioate moiety of the donating compound.

The invention as embodied in a diagnostic method for evaluating the proliferative state of a transformed cell may be performed on any transformed cell which contains a CDI capable of interacting with and/or capable of being inactivated by an HPV E7 oncoprotein. The diagnostic method is preferably performed on biopsied tissue which includes both transformed and untransformed cells, so that control cells are available which are substantially homogeneic with the transformed cell. In accordance with the invention, "substantially homogeneic" is defined as being derived from the same organism. The transformed and untransformed cells are separated from each other using known methods, such as Ficoll gradient separation or fluorescence-activated cell sorting. An extract or lysate may be made of the transformed cell, and a parallel extract or lysate is made of the untransformed cell. Cyclin/cyclin-dependent kinase complexes are isolated from the lysates as described above, and aliquotted. Aliquots of the transformed and untransformed cell cyclin/cyclin-dependent kinase complexes are incubated with an I-IPV E7 oncoprotein, and appropriate controls are included. The kinase activities of the cyclin/cyclin-dependent kinase complexes in the presence of the HPV E7 oncoprotein are measured as described above and compared to those of control aliquots which do not contain the HPV E7 oncoprotein. In accordance with the present invention, the kinase activity of a proliferating transformed cell will be substantially greater than that of the substantially homogeneic untransformed cell.

Alternatively the biopsy tissue containing the transformed and untransformed cells are fixed as for immunohistochemical staining using known methods. The fixed tissue is serially sectioned using known methods. Cyclin/cyclin-dependent kinase complexes are detected using polyclonal antibodies specific for a cyclin or for its specifically associated cyclin dependent kinase, or preferably using one or more monoclonal antibodies specific for a cyclin or for its specifically associated cyclin dependent kinase. An HPV E7 oncoprotein is added to the fixed tissues, and allowed to interact with the CDIs in the fixed tissues. Unbound E7 is removed from the fixed tissue, and the interaction between the CDI present in the fixed tissue and HPV E7 oncoprotein is measured, for example, using an antibody specific for HPV E7 oncoprotein.

The invention is also embodied as a method of inhibiting growth of an HPV-infected cell or hyperplastic lesion comprising administering to the cell a therapeutically effective amount of a compound that interferes with the ability of HPV oncoprotein E7 to interact with a CDI. As used herein, an "HPV-infected cell" is defined as a cell containing one or more DNA sequences characteristic of an HPV strain, including a DNA sequence encoding the E7 oncoprotein. As used herein, a "hyperplastic lesion" is defined as being composed of one or more cells containing one or more DNA sequences characteristic of a high-risk HPV strain, including a DNA sequence encoding the E7 oncoprotein. Further as defined herein, the term "therapeutically effective amount" means the total amount of the compound that is sufficient to show a meaningful amount of growth inhibition for the HPV-infected cell. When the HPV-infected cell is contained within a tumor, the term "therapeutically effective amount" additionally means the total amount of each active component of a pharmaceutical composition containing the compound to show any amount of inhibition of tumor growth.

In practicing the invention's method of inhibiting growth of an HPV-infected cell, a therapeutically effective amount of the compound that interferes with the ability of HPV oncoprotein E7 to interact with and/or inactivate a CDI (hereinafter "the inhibitory compound") is administered to a cell or to a lesion within a mammal, said lesion containing HPV genes or HPV antigens, including the E7 oncoprotein. The inhibitory compound may be administered either alone or in combination with other therapies such as chemotherapeutic agents, radiation therapy, or in combination with treatments employing one or more cytokines, lymphokines, or other hematopoietic factors. When co-administered with one or more cytokines, lymphokines, or other hematopoietic factors, the inhibitory compound may be administered either simultaneously with the cytokines, lymphokines, or other hematopoietic factors, or sequentially. If administered sequentially, the attending physician will determine the appropriate sequence of administering the inhibitory compound in combination with cytokines, lymphokines, or other hematopoietic factors.

Administration of the inhibitory compound in accordance with the method of the present invention can be carried out in a variety of conventional ways, such as oral ingestion, inhalation, or cutaneous, subcutaneous, or intravenous injection.

When a therapeutically effective amount of the inhibitory compound is administered orally, the compound will be in the form of a tablet, capsule, powder, solution or elixir. When administered in tablet form, the pharmaceutical composition used in this embodiment of the invention may additionally contain a solid carrier such as a gelatin or an adjuvant. The tablet, capsule, and powder contain from about 5 to 95% of the inhibitory compound and preferably from about 25 to 90% of the inhibitory compound. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the inhibitory compound and preferably from about 1 to 50% of the inhibitory compound.

When a therapeutically effective amount of the inhibitory compound is administered by intravenous, cutaneous or subcutaneous injection, the inhibitory compound will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the inhibitory compound, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition used in the therapeutic method of the present invention may also contain stabilizers, preservatives, buffers, antioxidants, or other additives known to those of skill in the art.

The amount of inhibitory compound in the pharmaceutical composition used in the therapeutic method of the present invention will depend upon the nature and severity of the condition being treated, and on the nature of prior treatments which the patient has undergone. Ultimately, the attending physician will decide the amount of inhibitory compound with which to treat each individual patient. Initially, the attending physician will administer low doses of the inhibitory compound and observe the patient's response. Larger doses of inhibitory compound may be administered until the optimal therapeutic effect is obtained for the patient, and at that point the dosage is not increased further. It is contemplated that the various pharmaceutical compositions used to practice the method of the present invention should contain about 0.1 μg to about 100 mg of inhibitory compound per kg body weight.

The duration of intravenous therapy in accordance with the present invention will vary, depending on the severity of the disease being treated and the condition and potential idiosyncratic response of each individual patient. It is contemplated that the duration of each application of the inhibitory compound will be in the range of 12 to 24 hours of continuous intravenous administration. Ultimately the attending physician will decide on the appropriate duration of intravenous therapy with an inhibitory compound in accordance with the present invention.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. A method of evaluating the proliferative state of a human papillomavirus transformed cell which comprises:

a. isolating cyclin/cyclin-dependent kinase complexes comprising the p21$^{CIP1}$ protein from the cell, and dividing said complexes into a plurality of aliquots;

b. adding human papilloma virus E7 oncoprotein to at least one aliquot from step a, wherein E7 oncoprotein interacts with the p21$^{CIP1}$ protein in the complexes of step a;

c. isolating an untransformed cell which is substantially homogeneic with the transformed cell;

d. isolating cyclin/cyclin-dependent kinase complexes from the untransformed cell of step c, and dividing said complexes into a plurality of aliquots;

e. adding human papilloma virus E7 oncoprotein to at least one aliquot from step d, wherein E7 oncoprotein interacts with the p21$^{CIP1}$ protein in the complexes of step d; and f. measuring the kinase activities of the respective aliquots, wherein a proliferating transformed cell is characterized by a greater kinase activity in comparison to the kinase activity of the substantially homogeneic untransformed cell.

* * * * *